United States Patent [19]

Takahashi et al.

[11] Patent Number: 5,138,104
[45] Date of Patent: Aug. 11, 1992

[54] PROCESS FOR PRODUCING DIHYDRIC PHENOLS

[75] Inventors: Katsuji Takahashi; Misao Uohama; Takayuki Akiyama, all of Chiba, Japan

[73] Assignee: Dainippon Ink and Chemicals, Inc., Tokyo, Japan

[21] Appl. No.: 735,582

[22] Filed: Jul. 25, 1991

[30] Foreign Application Priority Data

Jul. 26, 1990 [JP] Japan .................. 2-198745

[51] Int. Cl.$^5$ .............................................. C07C 37/60
[52] U.S. Cl. ...................................... 568/771; 568/768
[58] Field of Search ........................... 568/771, 268

[56] References Cited

U.S. PATENT DOCUMENTS

| | | | |
|---|---|---|---|
| 4,072,722 | 2/1978 | Umemura et al. | 260/261 |
| 4,078,006 | 3/1978 | Umemura et al. | 260/261 |
| 4,214,105 | 7/1980 | Seifert et al. | 568/771 |
| 4,223,165 | 9/1991 | Jouffret | 568/771 |

FOREIGN PATENT DOCUMENTS

| | | |
|---|---|---|
| 2138735 | 1/1973 | Fed. Rep. of Germany ...... 568/771 |
| 2514743B2 | 2/1981 | Fed. Rep. of Germany . |

OTHER PUBLICATIONS

Patent Abstracts of Japan, unexamined applications, C section, vol. 1, Nos. 102, Sep. 10, 1977, Kokai-No. 52-65232, 52-65233.

*Primary Examiner*—Werren B. Lone
*Attorney, Agent, or Firm*—Armstrong, Nikaido, Marmelstein, Kubovcik & Murray

[57] ABSTRACT

A process for producing dihydric phenols is disclosed. The process comprises reacting a phenol with a ketone peroxide or a combination of a ketone and hydrogen peroxide in the presence of a compound having at least one P-S bond. Dihydric phenols can be produced in high yield without requiring neutralization after the reaction.

10 Claims, No Drawings

PROCESS FOR PRODUCING DIHYDRIC PHENOLS

FIELD OF THE INVENTION

This invention relates to a process for producing dihydric phenols, e.g., catechol and hydroquinone, which are useful as starting materials for pharmaceuticals, agricultural chemicals, perfumes, and the like.

BACKGROUND OF THE INVENTION

Processes for producing dihydric phenols, e.g., catechol and hydroquinone, by hydroxylation of phenols include so-called ketone peroxide processes comprising reacting a phenol with a ketone peroxide in the presence of a sulfuric acid catalyst which are known to attain the highest yield (see U.S. Pat. Nos. 4,078,006).

Any of the known ketone peroxide processes, however, is still unsatisfactory in view of the yield and ease of isolation of the product. For example, use a large quantity of a sulfate as a catalyst in these processes not only makes it difficult to separate the catalyst from the product but requires a neutralization step. If the amount of the sulfate to be used is reduced, the yield of the product decreases. When in using sulfuric acid as a catalyst, the yield reached is low regardless of its amount, and a neutralization step is still needed.

SUMMARY OF THE INVENTION

An object of the present invention is to provide a process for producing dihydric phenols in high yield, which requires no neutralization after the reaction thereby allowing to effect reductions of the size of a reaction apparatus and the cost of production.

The inventors have conducted extensive investigations in the light of the above-mentioned present circumstances and found as a result that the above object of the present invention is accomplished by reacting a phenol with a ketone peroxide or a combination of a ketone and hydrogen peroxide in the presence of a compound having at least one P-S bond and thus reached the present invention.

The present invention relates to a process for producing a dihydric phenol comprising reacting a phenol with a ketone peroxide or a combination of a ketone and hydrogen peroxide in the presence of a compound having at least one P-S bond.

DETAILED DESCRIPTION OF THE INVENTION

For the sake of convenience of explanation, the process according to the present invention is divided into two modes according to the type of the oxidizing agent for hydroxylation of the phenolic nucleus:-(1) a process of using a ketone and hydrogen peroxide, and (2) a process of using a ketone peroxide.

Process (1) can be carried out according to either (1-a) a mode in which a ketone and hydrogen peroxide are previously mixed together and then added to a mixture of a phenol and a compound having at least one P-S bond to conduct a reaction for a period of from 5 minutes to 3 hours, followed by isolation or (1-b) a mode in which hydrogen peroxide is added to a mixture of a phenol, a ketone, and a compound having at least one P-S bond to conduct a reaction for a period of from 5 minutes to 3 hours, followed by isolation. In either of modes (1-a) and (1-b), while the addition operation may be performed continuously or intermittently, it is recommended to make the addition all at once in the shortest possible time for obtaining a high yield.

Process (2) can be carried out by adding dropwise a ketone peroxide to a mixed solution of a phenol and a compound having at least one P-S bond, allowing the mixture to react for a period of form 5 minutes to 3 hours, and isolating the product. In process (2), too, the addition is preferably done through single operation in the shortest possible time.

The compound having at least one P-S bond which can be used in the present invention include those having at least one P-S single bond and those having at least one P-S coordinate bond, e.g., phosphine sulfides and $P_4S_{10}$. The latter compounds are preferred from the viewpoint of yield.

Specific examples of the compounds having at least one P-S single bond include di(arylthio)phosphinic acids, e.g., di(phenylthio)phosphinic acid aniline salt; di(alkylthio)phosphinic acids, e.g., di(n-butylthio)phosphinic acid aniline salt; and trialkyl trithiophosphites, e.g., trilauryl trithiophosphite.

Specific examples of the phosphine sulfides include dithiophosphoric acid esters, e.g., diethyl dithiophosphate, dithiophosphoric acid O,O-diethyl ester, tri-n-butyl tetrathiophosphate, thiophosphonic acid O-phenyl-O,O-diethyl ester, and diethoxythiophosphonic acid; dithiadiphosphethane disulfides, e.g., 2,4-bis(4-methoxyphenyl)-1,3-dithia-2,4-diphosphethane-2,4-disulfide, and 1,3-dithia-2,4-[2,4-bis(2,6-dioxo-4,4-dimethyl)]dicyclophosphethane; dithiadiphosphethane trisulfides, e.g., tetra(n-butoxy)thiophosphoryl trisulfide, tetra(2-ethylhexanoyl)thiophosphoryl trisulfide, and di(n-butoxy-2-ethylhexanoyl)thiophosphoryl trisulfide; triphenylphosphine sulfide, tetramethyldiphosphine disulfide, etc. The P S bond is sometimes represented by a P=S double bond.

$P_4S_{10}$ is a compound called tetraphosphorus decasulfide or phosphorus pentasulfide.

The amount of the compound having at least one P-S bond to be used is not particularly critical. A suitable amount for obtaining a sufficient reaction rate usually ranges from 0.0001 to 1 part, and preferably from 0.001 to 0.01 part, by weight per 100 parts by weight of the phenol to be used for the reaction.

The phenol which can be used in the present invention is not particularly limited and includes, for example, phenol, anisole, o-cresol, p-cresol, o-chlorophenol, p-chlorophenol, o-bromophenol, p-bromophenol, o-methoxyphenol, p-methoxyphenol, o-ethylphenol, p-ethylphenol, o-(isopropyl)phenol, p-(isopropyl)phenol, o-(n-propyl)phenol, p-(n-propyl)phenol, o-(n-butyl)-phenol, p-(n-butyl)phenol, o-(isobutyl)phenol, p-(isobutyl)phenol, o-(t-butyl)phenol, and p-(t-butyl)-phenol.

The ketone to be used together with hydrogen peroxide according to process (1) is not particularly limited and includes compounds represented by formula (I):

wherein $R_1$ and $R_2$, which may be the same or different, each represent an alkyl group having up to 12 carbon atoms or an aryl group, or they are taken together to form a ring.

Specific examples of the ketone are methyl isobutyl ketone, methyl ethyl ketone, acetone, cyclohexanone, and acetophenone, with methyl isobutyl ketone being preferred.

Hydrogen peroxide may be anhydrous or aqueous but is preferably used as aqueous hydrogen peroxide for its ease of handling. The concentration of aqueous hydrogen peroxide, while not being limited, is preferably as high as possible, and particularly 60% by weight or higher.

The amount of the ketone to be used is not particularly limited but preferably ranges from 0.01 to 10 mols per mol of hydrogen peroxide.

The ketone peroxide which can be used in process (2) is not particularly limited and includes, for example, compounds represented by formula (II):

wherein $R_1$ and $R_4$, which may be the same or different, each represent an alkyl group having up to 12 carbon atoms or an aryl group, or they are taken together to form a ring.

Specific examples of the ketone peroxide include methyl isobutyl ketone peroxide, diisobutyl ketone peroxide, acetone peroxide, and acetophenone peroxide, with methyl isobutyl ketone peroxide being preferred.

The amount of the hydrogen peroxide or ketone peroxide to be used is not particularly critical but preferably ranges from 0.01 to 1.0 mol per mol of the phenol from the viewpoint of yield and inhibition of side reactions such as oxidation of the dihydric phenol produced.

The reaction temperature preferably ranges from 50° to 200° C., though varying depending on the activity of the compound having at least one P-S bond and the reactivity of the phenol to be hydroxylated. To ensure a sufficient reaction rate, a range of from 80° to 150° C. is more preferred. The reaction temperature may be adjusted by increasing or decreasing the amount of the catalyst to be used.

The reaction time preferably ranges from 5 minutes to 3 hours, and more preferably ranges from 15 minutes to 60 minutes.

The reaction may be performed without a solvent, or, if desired, an inert solvent may be employed. Further, the reaction may be conducted either batchwise or continuously (for example, by continuously feeding starting materials to a reactor as described in European Patent Publication 230625).

Solvents which can be used in the reaction include aliphatic hydrocarbons, e.g., n-pentane and cyclohexane; ethers, e.g., isopropyl ether, tetrahydrofuran, and dioxane; and halogenated hydrocarbons, e.g., dichloroethane and tetrachloroethane.

After completion of the reaction, the produced dihydric phenols can be isolated from the reaction mixture by removing the solvent and unreacted starting ketone and phenol by distillation and further continuing the distillation. The compound having at least one P-S bond can be separated by filtration, or it is thermally decomposed by distillation and thereby separated without being incorporated into the dihydric phenols produced.

The unreacted ketone and phenol recovered by distillation can be reused for the next reaction.

According to the present invention, use of the specific compound having at least one P-S bond as a catalyst makes it possible to produce dihydric phenols in high yields. In addition, the necessity for neutralization that has been always required in conventional processes can be precluded, thus reducing the production process involved.

Where methyl isobutyl ketone or methyl isobutyl ketone peroxide is used as a ketone or a ketone peroxide in the production of dihydric phenols according to ketone peroxide processes, the reaction is generally accompanied by by-production of isobutyl aldehyde, isobutyl alcohol, etc., which are incorporated into the isolated product in a trace amount. The process of the present invention is characterized by by-production of 2,4,4'-trihydroxybiphenyl ether in addition to the above-described by-products, which is observed incorporated into the isolated product in a trace amount. Therefore, the process of the present invention is distinguishable by the presence of this characteristic by-product. For example, the isolated product obtained by a ketone peroxide process using sulfuric acid as a catalyst is observed to contain a trace amount of nucleus-coupling compounds, e.g., 2,4,4'-trihydroxybiphenyl but no 2,4,4'-trihydroxybiphenyl ether.

The present invention is now illustrated in greater detail with reference to Examples, but it should be understood that the present invention is not deemed to be limited thereto. In Examples, all the mole percents for yields are based on hydrogen peroxide.

EXAMPLES 1 TO 12

In a 300 ml four-necked flask equipped with a stirrer, a condenser, and a thermometer were charged 65.8 g (0.7 mol) of phenol, 3.5 g (0.035 mol) of methyl isobutyl ketone, and 50 mg of each of the compounds shown in Table 1 below as a catalyst. The mixture was heated to 100° C., and 1.98 g (0.035 mol) of 60 wt % aqueous hydrogen peroxide was added thereto, followed by stirring for 30 minutes. The resulting reaction mixture was analyzed by gas chromatography to obtain yields of catechol and hydroquinone. The results obtained are shown in Table 1.

EXAMPLE 13

In a 300 ml four-necked flask equipped with a stirrer, a condenser, and a thermometer were charged 65.8 g (0.7 mol) of phenol and 50 mg of $P_4S_{10}$ as a catalyst. The mixture was heated to 100° C., and 8.5 g of a methyl isobutyl ketone solution containing 4.1 g (0.035 mol) of methyl isobutyl ketone peroxide was added thereto, followed by stirring for 30 minutes. The reaction mixture was analyzed by gas chromatography to obtain yields of catechol and hydroquinone. The results obtained are shown in Table 1.

EXAMPLE 14

The same procedures of Example 13 were repeated, except for replacing $P_4S_{10}$ with $(C_2H_5O)_2P(=S)SH$. The results obtained are shown in Table 1.

COMPARATIVE EXAMPLES 1 TO 3

The same procedures of Example 1 were repeated, except for using 50 mg of sulfuric acid or a salt thereof as a catalyst as shown in Table 1. After each reaction, the reaction mixture required neutralization. The results obtained are shown in Table 1.

TABLE 1

| Example No. | Catalyst | Yield (mol %) Catechol | Yield (mol %) Hydroquinone | Yield (mol %) Total | Catechol/ Hydroquinone |
| --- | --- | --- | --- | --- | --- |
| Example 1 | $P_4S_{10}$ | 52.2 | 37.6 | 89.8 | 1.39 |
| Example 2 | $[(CH_3)_2C(CH_2O)_2P(=S)]_2S$*1 | 51.8 | 39.8 | 91.6 | 1.30 |
| Example 3 | $Ph_3P=S$*2 | 52.9 | 38.4 | 91.3 | 1.38 |
| Example 4 | TBTP*3 | 51.8 | 38.4 | 90.2 | 1.35 |
| Example 5 | TEHTP*4 | 51.7 | 38.5 | 90.2 | 1.34 |
| Example 6 | TBETP*5 | 51.9 | 38.4 | 90.3 | 1.35 |
| Example 7 | $(C_2H_5O)_2P(=S)SH$*6 | 52.3 | 37.9 | 90.2 | 1.38 |
| Example 8 | $[p\text{-}CH_3OC_6H_4P(=S)S]_2$*7 | 52.0 | 38.2 | 90.2 | 1.36 |
| Example 9 | $(n\text{-}BuS)_3P=S$*8 | 51.6 | 39.0 | 90.6 | 1.32 |
| Example 10 | $(C_2H_5O)_2P(=S)OPH$*9 | 50.6 | 39.5 | 90.1 | 1.28 |
| Example 11 | $(CH_3)_2P(=S)P(=S)(CH_3)_2$*10 | 51.1 | 38.8 | 89.9 | 1.32 |
| Example 12 | $(C_2H_5O)_2P(=S)OH$*11 | 50.6 | 39.0 | 89.6 | 1.30 |
| Example 13 | $P_4S_{10}$ | 52.0 | 37.6 | 89.6 | 1.38 |
| Example 14 | $(C_2H_5O)_2P(=S)SH$*6 | 52.0 | 37.4 | 89.4 | 1.39 |
| Comparative Example 1 | $H_2SO_4$ | 47.2 | 32.4 | 79.6 | 1.46 |
| Comparative Example 2 | $KHSO_4$ | 44.1 | 27.1 | 71.2 | 1.63 |
| Comparative Example 3 | $NaHSO_4$ | 43.0 | 24.9 | 67.9 | 1.73 |

Note:
*1: 1,3-Dithia-2,4-[2,4-bis(2,6-dioxo-4,4-dimethyl)]cicyclophosphethane
*2: Triphenylphosphine sulfide
*3: Tetra(n-butoxy)thiophosphoryl trisulfide
*4: Tetra(2-ethylhexanoyl)thiophosphoryl trisulfide
*5: Di(n-butoxy-2-ethylhexanoyl)thiophosphoryl trisulfide
*6: Dithiophosphoric acid O,O-diethyl ester
*7: 2,4-Bis(4-methoxyphenyl)-1,3-dithia-2,4-diphosphethane-2,4-disulfide
*8: Tri-n-butyl tetrathiophosphate
*9: Thiophosphonic acid O-phenyl-O,O-diethyl ester
*10: Tetramethyldiphosphine disulfide
*11: Diethoxythiophosphonic acid

EXAMPLES 15 TO 17

The same procedures of Example 1 were repeated, except for using each of the compounds shown in Table 2 below as a ketone. The results obtained are also shown in Table 2.

EXAMPLE 18

The same procedures of Example 7 were repeated, except for using acetone as a ketone. The results obtained are shown in Table 2.

TABLE 2

| Example No. | Ketone | Yield (mol %) Catechol | Yield (mol %) Hydroquinone | Yield (mol %) Total | Catechol/ Hydroquinone |
| --- | --- | --- | --- | --- | --- |
| 15 | acetone | 50.7 | 36.8 | 87.5 | 1.38 |
| 16 | methyl ethyl ketone | 50.4 | 36.2 | 86.6 | 1.39 |
| 17 | diisobutyl ketone | 50.7 | 37.2 | 87.9 | 1.36 |
| 18 | acetone | 51.4 | 37.4 | 38.8 | 1.37 |

TABLE 3

| Example No. | Phenol | Yield (mol %) Ortho Compound | Yield (mol %) Other Products | Total | Ortho compound/ Para Compound |
| --- | --- | --- | --- | --- | --- |
| 19 | p-(t-butyl)phenol | t-butylcatechol 77.4 | 2,4-di-t-butylphenol 8.2 | 85.6 | — |
| 20 | p-cresol | 4-methylcatechol 72.6 | — | 72.6 | — |
| 21 | anisole | guaiacol 36.6 | methoquinone 34.4 | 71.0 | 1.06 |
| 22 | p-(t-butyl)phenol | t-butylcatechol 76.8 | 2,4-di-t-butylphenol 4.4 | 81.2 | — |

EXAMPLES 19 TO 21

The same procedures of Example 1 were repeated, except for using each of the compounds shown in Table 3 below as a phenol. The results obtained are also shown in Table 3.

EXAMPLE 22

The same procedures of Example 7 were repeated, except for using p-(t-butyl)phenol as a phenol. The results obtained are shown in Table 3.

Incidentally, when the same procedures of Examples 17 to 19 were repeated, except for using 50 mg of sulfuric acid as a catalyst, the yield obtained was markedly lower than those in Examples 17 to 19, and a neutralization step was needed.

While the invention has been described in detail and with reference to specific examples thereof, it will be apparent to one skilled in the art that various changes and modifications can be made therein without departing from the spirit and scope thereof.

What is claimed is:

1. A process for producing a dihydric phenol comprising reacting a phenol with a ketone peroxide or a combination of a ketone and hydrogen peroxide in the presence of a compound having at least one P-S bond selected from the group consisting of di(arylthio)phosphinic acids, di(alkylthio)phosphinic acids, trialkyltrithiophosphites, dithiophosphoric acid esters, dithiadiphosphethane disulfides, dithiadiphosphethane trisulfides, triarylphosphine sulfides, tetraalkyldiphosphine disulfides and $P_4S_{10}$, at a temperature of from 50° to 200° C.

2. A process as claimed in claim 11, wherein said compound having at least one P-S bond is selected from the group consisting of di(arylthio)phosphic acids, di(alkylthio)phosphinic acids, trialkyl trithiophosphites, dithiophosphoric acid esters, dithiadiphosphethane disulfides, dithiadiphosphethane trisulfides, triphenylphosphine sulfide, tetramethyldiphosphine disulfides and $P_4P_{10}$.

3. A process as claimed in claim 2, wherein said compound having at least one P-S bond is selected from the group consisting of dithiophosphoric acid esters, dithiadiphosphethane disulfides, dithiadiphosphethane trisulfides, triphenylphosphine sulfide, tetramethyliphosphine disulfides and $P_4S_{10}$.

4. A process as claimed in claim 3, wherein said compound having at least one P-S bond is selected from the group consisting of diethyl dithiophosphate, dithiophosphoric acid O,O-diethyl ester, tri-n-butyl tetrathtiophosphate, thiophosphonic acid O-phenyl-O,O-diethyl ester, diethoxythiophosphonic acid, 2,4-bis(4-methoxyphenyl)-1,3-dithia-2,4-diphosphethane-2,4-disulfide, 1,3-dithia-2,4-[2,4-bis(2,6-dioxo-4,4-(dimethyl)]dicyclophosphethane, tetra(n-butoxy)thiophosphoryl trisulfide, di(n-butoxy-2-ethylhexanoyl)thiophosphoryl trisulfide, tripheylphosphine sulfide and tetramethyldiphosphine disulfide.

5. A process as claimed in claim 3, wherein said compound having at least one P-S bond is $P_4S_{10}$.

6. A process as claimed in claim 1, wherein said ketone peroxide is methyl isobutyl ketone peroxide.

7. A process as claimed in claim 1, wherein said ketone is methyl isobutyl ketone.

8. A process as claimed in claim 1, wherein said compounding having at least one P-S bond is used in an amount of from 0.001 to 0.01 by weight per 100 parts by weight of the phenol.

9. A process as claimed in claim 1, wherein said ketone peroxide is used in an amount of from 0.01 to 1.0 mol per mol of phenol.

10. A process as claimed in claim 1, wherein said hydrogen peroxide is used in an amount of from 0.01 to 1.0 mol per mol of the phenol and said ketone is used in an amount of from 0.01 to .10 mols per mol of the hydrogen peroxide.

* * * * *